United States Patent
Ruff

(10) Patent No.: US 8,246,652 B2
(45) Date of Patent: *Aug. 21, 2012

(54) SUTURE WITH A POINTED END AND AN ANCHOR END AND WITH EQUALLY SPACED YIELDABLE TISSUE GRASPING BARBS LOCATED AT SUCCESSIVE AXIAL LOCATIONS

(75) Inventor: Gregory L. Ruff, Chapel Hill, NC (US)

(73) Assignee: Ethicon, Inc., Somerville, NJ (US)

( * ) Notice: Subject to any disclaimer, the term of this patent is extended or adjusted under 35 U.S.C. 154(b) by 48 days.

This patent is subject to a terminal disclaimer.

(21) Appl. No.: 12/849,946

(22) Filed: Aug. 4, 2010

(65) Prior Publication Data

US 2010/0298869 A1    Nov. 25, 2010

Related U.S. Application Data

(63) Continuation of application No. 11/968,494, filed on Jan. 2, 2008, now Pat. No. 7,806,908, which is a continuation of application No. 11/747,085, filed on May 10, 2007, now abandoned, which is a continuation of application No. 10/420,119, filed on Apr. 21, 2003, now Pat. No. 7,226,468, which is a continuation of application No. 09/629,428, filed on Jul. 31, 2000, now abandoned, which is a continuation of application No. 08/324,529, filed on Oct. 18, 1994, now Pat. No. 6,241,747, which is a continuation-in-part of application No. 08/055,989, filed on May 3, 1993, now abandoned.

(51) Int. Cl.
*A61B 17/03* (2006.01)

(52) U.S. Cl. .......... 606/216; 606/232; 606/213
(58) Field of Classification Search .......... 606/151, 606/153, 155, 213, 216, 217, 228, 230
See application file for complete search history.

(56) References Cited

U.S. PATENT DOCUMENTS

| | | |
|---|---|---|
| 709,392 A | 9/1902 | Brown |
| 733,723 A | 7/1903 | Lukens |
| 789,401 A | 5/1905 | Acheson |
| 816,026 A | 3/1906 | Meier |

(Continued)

FOREIGN PATENT DOCUMENTS

BE    1014364    9/2003

(Continued)

OTHER PUBLICATIONS

International Search Report for PCT/US2007/074658 dated Jun. 12, 2007, 3 pages.

(Continued)

*Primary Examiner* — Michael Peffley
(74) *Attorney, Agent, or Firm* — Melissa J. Szanto

(57) ABSTRACT

A tissue connector has a first pointed end, an anchor end, a body with a periphery and a plurality of barbs projecting from said periphery of said body. The plurality of barbs are yieldable in one direction, which direction is the direction of motion of the first pointed end through tissue, and are rigid in an opposite direction, which is in the direction of the anchor end. At axial locations of said body, said barbs are about equally located about the periphery of said body. At axial locations on a cylindrical periphery of the body barbs are locate at about 120 degree spacings. The barbs are conically shaped.

16 Claims, 4 Drawing Sheets

U.S. PATENT DOCUMENTS

| | | | |
|---|---|---|---|
| 879,758 A | 2/1908 | Foster | |
| 1,142,510 A | 6/1915 | Engle | |
| 1,248,825 A | 12/1917 | Dederer | |
| 1,321,011 A | 11/1919 | Cottes | |
| 1,558,037 A | 10/1925 | Morton | |
| 1,728,316 A | 9/1929 | Wachenfeldt | |
| 1,886,721 A | 11/1932 | O'Brien | |
| 2,094,578 A | 10/1937 | Blumenthal | |
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,472,009 A | 5/1949 | Gardner | |
| 2,572,936 A | 10/1951 | Kulp | |
| 2,684,070 A | 7/1954 | Kelsey | |
| 2,779,083 A | 1/1957 | Eaton | |
| 2,814,296 A | 11/1957 | Everett | |
| 2,817,339 A | 12/1957 | Sullivan | |
| 2,866,256 A | 12/1958 | Matlin | |
| 2,910,067 A | 10/1959 | White | |
| 2,988,028 A | 6/1961 | Alcamo | |
| 3,003,155 A | 10/1961 | Mielzynski | |
| 3,068,869 A | 12/1962 | Shelden | |
| 3,068,870 A | 12/1962 | Levin | |
| 3,123,077 A | 3/1964 | Alcamo | |
| 3,166,072 A | 1/1965 | Sullivan | |
| 3,187,752 A | 6/1965 | Glick | |
| 3,206,018 A | 9/1965 | Lewis | |
| 3,209,652 A | 10/1965 | Burgsmueller | |
| 3,209,754 A | 10/1965 | Brown | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling | |
| 3,385,299 A | 5/1968 | Le Roy | |
| 3,494,006 A * | 2/1970 | Brumlik | 24/447 |
| 3,525,340 A | 8/1970 | Gilbert | |
| 3,527,223 A | 9/1970 | Shein | |
| 3,545,608 A | 12/1970 | Berger | |
| 3,570,497 A | 3/1971 | Lemole | |
| 3,586,002 A | 6/1971 | Wood | |
| 3,608,095 A | 9/1971 | Barry | |
| 3,608,539 A | 9/1971 | Miller | |
| 3,646,615 A | 3/1972 | Ness | |
| 3,683,926 A | 8/1972 | Suzuki | |
| 3,700,433 A | 10/1972 | Duhl | |
| 3,716,058 A * | 2/1973 | Tanner, Jr. | 606/221 |
| 3,720,055 A | 3/1973 | deMestral | |
| 3,825,010 A | 7/1974 | McDonald | |
| 3,833,972 A | 9/1974 | Brumlik | |
| 3,845,641 A | 11/1974 | Waller | |
| 3,847,156 A | 11/1974 | Trumble | |
| 3,918,455 A | 11/1975 | Coplan | |
| 3,951,261 A | 4/1976 | Mandel | |
| 3,981,051 A | 9/1976 | Brumlik | |
| 3,981,307 A | 9/1976 | Borysko | |
| 3,985,138 A | 10/1976 | Jarvik | |
| 3,985,227 A | 10/1976 | Thyen | |
| 4,006,747 A | 2/1977 | Kronenthal | |
| 4,008,303 A | 2/1977 | Glick | |
| 4,027,608 A | 6/1977 | Arbuckle | |
| 4,043,344 A | 8/1977 | Landi | |
| D246,911 S | 1/1978 | Bess, Jr. | |
| 4,069,825 A | 1/1978 | Akiyama | |
| 4,073,298 A | 2/1978 | Le Roy | |
| 4,137,921 A | 2/1979 | Okuzumi | |
| 4,198,734 A | 4/1980 | Brumlik | |
| 4,204,541 A | 5/1980 | Kapitanov | |
| 4,204,542 A | 5/1980 | Bokros | |
| 4,259,959 A | 4/1981 | Walker | |
| 4,300,424 A | 11/1981 | Flinn | |
| 4,313,448 A | 2/1982 | Stokes | |
| 4,316,469 A | 2/1982 | Kapitanov | |
| 4,317,451 A | 3/1982 | Cerwin | |
| 4,428,376 A | 1/1984 | Mericle | |
| 4,430,998 A | 2/1984 | Harvey | |
| 4,434,796 A | 3/1984 | Karapetian | |
| 4,454,875 A | 6/1984 | Pratt | |
| 4,467,805 A | 8/1984 | Fukuda | |
| 4,492,075 A | 1/1985 | Faure | |
| 4,493,323 A | 1/1985 | Albright | |
| 4,505,274 A | 3/1985 | Speelman | |
| 4,510,934 A | 4/1985 | Batra | |
| 4,531,522 A | 7/1985 | Bedi | |
| 4,532,926 A | 8/1985 | O'Holla | |
| 4,535,772 A | 8/1985 | Sheehan | |
| 4,548,202 A | 10/1985 | Duncan | |
| 4,553,544 A | 11/1985 | Nomoto | |
| 4,610,250 A | 9/1986 | Green | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards | |
| 4,676,245 A | 6/1987 | Fukuda | |
| 4,719,917 A | 1/1988 | Barrows | |
| 4,741,330 A | 5/1988 | Hayhurst | |
| 4,750,910 A | 6/1988 | Takayanagi | |
| 4,751,621 A | 6/1988 | Jenkins | |
| 4,776,337 A | 10/1988 | Palmaz | |
| 4,832,025 A | 5/1989 | Coates | |
| 4,841,960 A | 6/1989 | Garner | |
| 4,865,026 A | 9/1989 | Barrett | |
| 4,873,976 A * | 10/1989 | Schreiber | 606/213 |
| 4,887,601 A | 12/1989 | Richards | |
| 4,895,148 A | 1/1990 | Bays | |
| 4,898,156 A | 2/1990 | Gatturna | |
| 4,899,743 A | 2/1990 | Nicholson | |
| 4,900,605 A | 2/1990 | Thorgersen | |
| 4,905,367 A | 3/1990 | Pinchuk | |
| 4,930,945 A | 6/1990 | Arai | |
| 4,932,962 A | 6/1990 | Yoon | |
| 4,946,468 A | 8/1990 | Li | |
| 4,948,444 A | 8/1990 | Schutz | |
| 4,950,258 A | 8/1990 | Kawai | |
| 4,950,285 A | 8/1990 | Wilk | |
| 4,968,315 A | 11/1990 | Gatturna | |
| 4,976,715 A | 12/1990 | Bays | |
| 4,981,149 A | 1/1991 | Yoon | |
| 4,994,073 A | 2/1991 | Green | |
| 4,997,439 A | 3/1991 | Chen | |
| 5,002,550 A | 3/1991 | Li | |
| 5,002,562 A | 3/1991 | Oberlander | |
| 5,007,921 A | 4/1991 | Brown | |
| 5,007,922 A | 4/1991 | Chen | |
| 5,026,390 A | 6/1991 | Brown | |
| 5,037,422 A | 8/1991 | Hayhurst | |
| 5,041,129 A | 8/1991 | Hayhurst | |
| 5,046,513 A | 9/1991 | Gatturna | |
| 5,047,047 A | 9/1991 | Yoon | |
| 5,053,047 A * | 10/1991 | Yoon | 606/223 |
| 5,084,063 A | 1/1992 | Korthoff | |
| 5,089,010 A | 2/1992 | Korthoff | |
| 5,101,968 A | 4/1992 | Henderson | |
| 5,102,418 A | 4/1992 | Granger | |
| 5,102,421 A | 4/1992 | Anspach, Jr. | |
| 5,103,073 A | 4/1992 | Danilov | |
| 5,112,344 A | 5/1992 | Petros | |
| 5,123,911 A | 6/1992 | Granger | |
| 5,123,913 A | 6/1992 | Wilk | |
| 5,123,919 A | 6/1992 | Sauter | |
| 5,127,413 A | 7/1992 | Ebert | |
| 5,133,738 A | 7/1992 | Korthoff | |
| 5,141,520 A | 8/1992 | Goble | |
| 5,147,382 A | 9/1992 | Gertzman | |
| 5,156,788 A | 10/1992 | Chesterfield | |
| 5,176,692 A | 1/1993 | Wilk | |
| 5,179,964 A | 1/1993 | Cook | |
| 5,192,274 A | 3/1993 | Bierman | |
| 5,192,302 A | 3/1993 | Kensey | |
| 5,192,303 A | 3/1993 | Gatturna | |
| 5,197,597 A | 3/1993 | Leary | |
| 5,207,679 A | 5/1993 | Li | |

| Patent No. | Date | Name |
|---|---|---|
| 5,207,694 A | 5/1993 | Broome |
| 5,217,486 A | 6/1993 | Rice |
| 5,217,494 A | 6/1993 | Coggins |
| 5,222,508 A | 6/1993 | Contarini |
| 5,222,976 A | 6/1993 | Yoon |
| 5,224,946 A | 7/1993 | Hayhurst |
| 5,242,457 A | 9/1993 | Akopov |
| 5,246,441 A | 9/1993 | Ross |
| 5,249,673 A | 10/1993 | Sinn |
| 5,258,013 A | 11/1993 | Granger |
| 5,263,973 A | 11/1993 | Cook |
| 5,269,783 A | 12/1993 | Sander |
| 5,282,832 A | 2/1994 | Toso |
| 5,292,326 A | 3/1994 | Green |
| 5,306,288 A | 4/1994 | Granger |
| 5,306,290 A | 4/1994 | Martins |
| 5,320,629 A | 6/1994 | Noda |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin |
| 5,342,376 A | 8/1994 | Ruff |
| 5,342,395 A | 8/1994 | Jarrett |
| 5,352,515 A | 10/1994 | Jarrett |
| 5,354,271 A | 10/1994 | Voda |
| 5,354,298 A | 10/1994 | Lee |
| 5,358,511 A | 10/1994 | Gatturna |
| 5,372,146 A | 12/1994 | Branch |
| 5,374,268 A | 12/1994 | Sander |
| 5,374,278 A | 12/1994 | Chesterfield |
| 5,380,334 A | 1/1995 | Torrie |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | DiPalma |
| 5,417,691 A | 5/1995 | Hayhurst |
| 5,425,746 A | 6/1995 | Proto |
| 5,425,747 A | 6/1995 | Brotz |
| 5,437,680 A | 8/1995 | Yoon |
| 5,450,860 A | 9/1995 | O'Connor |
| 5,451,461 A | 9/1995 | Broyer |
| 5,462,561 A | 10/1995 | Voda |
| 5,464,427 A | 11/1995 | Curtis |
| 5,472,452 A | 12/1995 | Trott |
| 5,478,353 A | 12/1995 | Yoon |
| 5,480,403 A | 1/1996 | Lee |
| 5,480,411 A | 1/1996 | Liu |
| 5,484,451 A | 1/1996 | Akopov |
| 5,486,197 A | 1/1996 | Le |
| 5,494,154 A | 2/1996 | Ainsworth |
| 5,500,000 A | 3/1996 | Feagin |
| 5,500,991 A | 3/1996 | Demarest |
| 5,520,084 A | 5/1996 | Chesterfield |
| 5,520,691 A | 5/1996 | Branch |
| 5,522,845 A | 6/1996 | Wenstrom, Jr. |
| 5,531,760 A | 7/1996 | Alwafaie |
| 5,531,761 A | 7/1996 | Yoon |
| 5,531,790 A | 7/1996 | Frechet |
| 5,533,982 A | 7/1996 | Rizk |
| 5,536,582 A | 7/1996 | Prasad |
| 5,540,705 A | 7/1996 | Meade |
| 5,540,718 A | 7/1996 | Bartlett |
| 5,546,957 A | 8/1996 | Heske |
| 5,554,171 A | 9/1996 | Gatturna |
| 5,566,822 A | 10/1996 | Scanlon |
| 5,571,175 A | 11/1996 | Vanney |
| 5,571,216 A | 11/1996 | Anderson |
| 5,573,543 A | 11/1996 | Akopov |
| 5,584,859 A | 12/1996 | Brotz |
| 5,601,557 A | 2/1997 | Hayhurst |
| 5,626,590 A | 5/1997 | Wilk |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green |
| 5,647,874 A | 7/1997 | Hayhurst |
| 5,649,939 A | 7/1997 | Reddick |
| 5,653,716 A | 8/1997 | Malo |
| 5,662,714 A | 9/1997 | Charvin |
| 5,669,935 A | 9/1997 | Rosenman |
| D386,583 S | 11/1997 | Ferragamo |
| 5,683,417 A | 11/1997 | Cooper |
| 5,697,976 A | 12/1997 | Chesterfield |
| 5,702,462 A | 12/1997 | Oberlander |
| 5,709,692 A | 1/1998 | Mollenauer |
| 5,716,358 A | 2/1998 | Ochoa |
| 5,716,376 A | 2/1998 | Roby |
| 5,722,991 A | 3/1998 | Colligan |
| 5,723,008 A | 3/1998 | Gordon |
| 5,725,557 A | 3/1998 | Gatturna |
| 5,728,114 A | 3/1998 | Evans |
| 5,741,277 A | 4/1998 | Gordon |
| 5,763,411 A | 6/1998 | Edwardson |
| 5,765,560 A | 6/1998 | Verkerke |
| 5,779,719 A | 7/1998 | Klein |
| 5,782,864 A | 7/1998 | Lizardi |
| 5,807,403 A | 9/1998 | Beyar |
| 5,807,406 A | 9/1998 | Brauker |
| 5,810,853 A | 9/1998 | Yoon |
| 5,814,051 A | 9/1998 | Wenstrom, Jr. |
| 5,843,087 A | 12/1998 | Jensen |
| 5,843,178 A | 12/1998 | Vanney |
| 5,863,360 A | 1/1999 | Wood |
| 5,884,859 A | 3/1999 | Ma |
| 5,887,594 A | 3/1999 | LoCicero, III |
| 5,891,166 A | 4/1999 | Schervinsky |
| 5,893,856 A | 4/1999 | Jacob |
| 5,895,395 A | 4/1999 | Yeung |
| 5,895,413 A | 4/1999 | Nordstrom |
| 5,897,572 A | 4/1999 | Schulsinger |
| 5,899,911 A | 5/1999 | Carter |
| 5,916,224 A | 6/1999 | Esplin |
| 5,919,234 A | 7/1999 | Lemperle |
| 5,921,982 A | 7/1999 | Lesh |
| 5,925,078 A | 7/1999 | Anderson |
| 5,931,855 A | 8/1999 | Buncke |
| 5,935,138 A | 8/1999 | McJames, II |
| 5,938,668 A | 8/1999 | Scirica |
| 5,950,633 A | 9/1999 | Lynch |
| 5,954,747 A | 9/1999 | Clark |
| 5,968,097 A | 10/1999 | Frechet |
| 5,972,024 A | 10/1999 | Northrup, III |
| 5,984,933 A | 11/1999 | Yoon |
| 5,993,459 A | 11/1999 | Larsen |
| 6,001,111 A | 12/1999 | Sepetka |
| 6,012,216 A | 1/2000 | Esteves |
| 6,015,410 A | 1/2000 | Tormala |
| 6,024,757 A | 2/2000 | Haase |
| 6,027,523 A | 2/2000 | Schmieding |
| 6,039,741 A | 3/2000 | Meislin |
| 6,056,778 A | 5/2000 | Grafton |
| 6,063,105 A | 5/2000 | Totakura |
| 6,074,419 A | 6/2000 | Healy |
| 6,076,255 A | 6/2000 | Shikakubo |
| 6,083,244 A | 7/2000 | Lubbers |
| 6,102,947 A | 8/2000 | Gordon |
| 6,106,544 A | 8/2000 | Brazeau |
| D433,753 S | 11/2000 | Weiss |
| 6,146,406 A | 11/2000 | Shluzas |
| 6,146,407 A | 11/2000 | Krebs |
| 6,149,660 A | 11/2000 | Laufer |
| 6,163,948 A | 12/2000 | Esteves |
| 6,165,203 A | 12/2000 | Krebs |
| 6,168,633 B1 | 1/2001 | Shoher |
| 6,174,324 B1 | 1/2001 | Egan |
| 6,183,499 B1 | 2/2001 | Fischer |
| 6,187,095 B1 | 2/2001 | Labrecque |
| 6,206,908 B1 | 3/2001 | Roby |
| 6,235,869 B1 | 5/2001 | Roby |
| 6,241,747 B1 | 6/2001 | Ruff |
| 6,251,143 B1 | 6/2001 | Schwartz |
| 6,264,675 B1 | 7/2001 | Brotz |
| 6,267,772 B1 | 7/2001 | Mulhauser |
| 6,270,517 B1 | 8/2001 | Brotz |
| 6,315,788 B1 | 11/2001 | Roby |
| 6,319,231 B1 | 11/2001 | Andrulitis |
| 6,334,865 B1 | 1/2002 | Redmond |

| | | |
|---|---|---|
| 6,387,363 B1 | 5/2002 | Gruskin |
| 6,388,043 B1 | 5/2002 | Langer |
| 6,395,029 B1 | 5/2002 | Levy |
| D462,766 S | 9/2002 | Jacobs |
| 6,443,962 B1 | 9/2002 | Gaber |
| 6,463,719 B2 | 10/2002 | Dey |
| 6,471,715 B1 | 10/2002 | Weiss |
| 6,478,809 B1 | 11/2002 | Brotz |
| 6,485,503 B2 | 11/2002 | Jacobs |
| 6,491,701 B2 | 12/2002 | Tierney |
| 6,494,898 B1 | 12/2002 | Roby |
| 6,495,127 B1 | 12/2002 | Wallace |
| RE37,963 E | 1/2003 | Thal |
| 6,506,190 B1 | 1/2003 | Walshe |
| 6,511,488 B1 | 1/2003 | Marshall |
| 6,514,265 B2 | 2/2003 | Ho |
| 6,527,795 B1 | 3/2003 | Lizardi |
| 6,551,343 B1 | 4/2003 | Tormala |
| 6,554,802 B1 | 4/2003 | Pearson |
| 6,565,597 B1 | 5/2003 | Fearnot |
| 6,592,609 B1 | 7/2003 | Bonutti |
| 6,596,296 B1 | 7/2003 | Nelson |
| 6,599,310 B2 | 7/2003 | Leung |
| 6,607,541 B1 | 8/2003 | Gardiner |
| 6,610,078 B1 | 8/2003 | Bru-Magniez |
| 6,613,059 B2 | 9/2003 | Schaller |
| 6,613,254 B1 | 9/2003 | Shiffer |
| 6,616,982 B2 | 9/2003 | Merrill |
| 6,623,492 B1 | 9/2003 | Berube |
| 6,626,930 B1 | 9/2003 | Allen |
| 6,641,592 B1 | 11/2003 | Sauer |
| 6,641,593 B1 | 11/2003 | Schaller |
| 6,645,226 B1 | 11/2003 | Jacobs |
| 6,645,227 B2 | 11/2003 | Fallin |
| 6,648,921 B2 | 11/2003 | Anderson |
| 6,656,182 B1 | 12/2003 | Hayhurst |
| 6,689,153 B1 | 2/2004 | Skiba |
| 6,702,844 B1 | 3/2004 | Lazarus |
| 6,712,830 B2 | 3/2004 | Esplin |
| 6,716,234 B2 | 4/2004 | Grafton |
| 6,720,402 B2 | 4/2004 | Langer |
| 6,726,705 B2 | 4/2004 | Peterson |
| 6,746,443 B1 | 6/2004 | Morley |
| 6,746,458 B2 | 6/2004 | Cloud |
| 6,749,616 B1 | 6/2004 | Nath |
| 6,773,450 B2 | 8/2004 | Leung |
| 6,783,554 B2 | 8/2004 | Amara |
| 6,814,748 B1 | 11/2004 | Baker |
| 6,818,010 B2 | 11/2004 | Eichhorn |
| 6,838,493 B2 | 1/2005 | Williams |
| 6,848,152 B2 | 2/2005 | Genova |
| 6,852,825 B2 | 2/2005 | Lendlein |
| 6,858,222 B2 | 2/2005 | Nelson |
| 6,860,891 B2 | 3/2005 | Schulze |
| 6,860,901 B1 | 3/2005 | Baker |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman |
| 6,911,035 B1 | 6/2005 | Blomme |
| 6,911,037 B2 | 6/2005 | Gainor |
| 6,913,607 B2 | 7/2005 | Ainsworth |
| 6,921,811 B2 | 7/2005 | Zamora |
| 6,923,819 B2 | 8/2005 | Meade |
| 6,945,980 B2 | 9/2005 | Nguyen |
| 6,960,221 B2 | 11/2005 | Ho |
| 6,960,233 B1 | 11/2005 | Berg |
| 6,974,450 B2 | 12/2005 | Weber |
| 6,981,983 B1 | 1/2006 | Rosenblatt |
| 6,984,241 B2 | 1/2006 | Lubbers |
| 6,986,780 B2 | 1/2006 | Rudnick |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson |
| 7,037,984 B2 | 5/2006 | Lendlein |
| 7,048,748 B1 | 5/2006 | Ustuner |
| 7,056,331 B2 | 6/2006 | Kaplan |
| 7,056,333 B2 | 6/2006 | Walshe |
| 7,057,135 B2 | 6/2006 | Li |
| 7,070,610 B2 | 7/2006 | Im |
| 7,081,135 B2 | 7/2006 | Smith |
| 7,083,637 B1 | 8/2006 | Tannhauser |
| 7,083,648 B2 | 8/2006 | Yu |
| 7,107,090 B2 | 9/2006 | Salisbury |
| 7,112,214 B2 | 9/2006 | Peterson |
| 7,125,403 B2 | 10/2006 | Julian |
| 7,125,413 B2 | 10/2006 | Grigoryants |
| D532,107 S | 11/2006 | Peterson |
| 7,138,441 B1 | 11/2006 | Zhang |
| 7,141,302 B2 | 11/2006 | Mueller |
| 7,144,401 B2 | 12/2006 | Yamamoto |
| 7,144,412 B2 | 12/2006 | Wolf |
| 7,144,415 B2 | 12/2006 | Del Rio |
| 7,150,757 B2 | 12/2006 | Fallin |
| 7,156,858 B2 | 1/2007 | Schuldt-Hempe |
| 7,156,862 B2 | 1/2007 | Jacobs |
| 7,160,312 B2 | 1/2007 | Saadat |
| 7,166,570 B2 | 1/2007 | Hunter |
| 7,172,595 B1 | 2/2007 | Goble |
| 7,172,615 B2 | 2/2007 | Morriss |
| 7,186,262 B2 | 3/2007 | Saadat |
| 7,195,634 B2 | 3/2007 | Schmieding |
| 7,211,088 B2 | 5/2007 | Grafton |
| 7,214,230 B2 | 5/2007 | Brock |
| 7,217,744 B2 | 5/2007 | Lendlein |
| 7,225,512 B2 | 6/2007 | Genova |
| 7,226,468 B2 | 6/2007 | Ruff |
| 7,232,447 B2 | 6/2007 | Gellman |
| 7,244,270 B2 | 7/2007 | Lesh |
| 7,279,612 B1 | 10/2007 | Heaton |
| 7,297,142 B2 | 11/2007 | Brock |
| 7,322,105 B2 | 1/2008 | Lewis |
| 7,371,253 B2 | 5/2008 | Leung |
| 7,513,904 B2 | 4/2009 | Sulamanidze |
| 7,514,095 B2 | 4/2009 | Nelson |
| 7,582,105 B2 | 9/2009 | Kolster |
| 7,601,164 B2 | 10/2009 | Wu |
| 7,624,487 B2 | 12/2009 | Trull |
| 7,806,908 B2 | 10/2010 | Ruff |
| 2001/0011187 A1 | 8/2001 | Pavcnik |
| 2001/0018599 A1 | 8/2001 | D'Aversa |
| 2001/0039450 A1 | 11/2001 | Pavcnik |
| 2001/0044637 A1 | 11/2001 | Jacobs |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs |
| 2002/0029066 A1 | 3/2002 | Foerster |
| 2002/0069617 A1 | 6/2002 | Dey |
| 2002/0077448 A1 | 6/2002 | Antal |
| 2002/0077631 A1 | 6/2002 | Lubbers |
| 2002/0095164 A1 | 7/2002 | Andreas |
| 2002/0099394 A1 | 7/2002 | Houser |
| 2002/0111641 A1 | 8/2002 | Peterson |
| 2002/0111688 A1 | 8/2002 | Cauthen |
| 2002/0138009 A1 | 9/2002 | Brockway |
| 2002/0151980 A1 | 10/2002 | Cauthen |
| 2002/0173807 A1 | 11/2002 | Jacobs |
| 2002/0173822 A1 | 11/2002 | Justin |
| 2002/0179718 A1 | 12/2002 | Murokh |
| 2003/0014077 A1 | 1/2003 | Leung |
| 2003/0040795 A1 | 2/2003 | Elson |
| 2003/0041426 A1 | 3/2003 | Genova |
| 2003/0065360 A1 | 4/2003 | Jacobs |
| 2003/0065402 A1 | 4/2003 | Anderson |
| 2003/0069602 A1 | 4/2003 | Jacobs |
| 2003/0074021 A1 | 4/2003 | Morriss |
| 2003/0074023 A1 | 4/2003 | Kaplan |
| 2003/0078604 A1 | 4/2003 | Walshe |
| 2003/0088270 A1 | 5/2003 | Lubbers |
| 2003/0097150 A1 | 5/2003 | Fallin |
| 2003/0105489 A1 | 6/2003 | Eichhorn |
| 2003/0149447 A1 | 8/2003 | Morency |
| 2003/0158604 A1 | 8/2003 | Cauthen, III |
| 2003/0167072 A1 | 9/2003 | Oberlander |
| 2003/0203003 A1 | 10/2003 | Nelson |

| Publication No. | Date | Name |
|---|---|---|
| 2003/0204195 A1 | 10/2003 | Keane |
| 2003/0229361 A1 | 12/2003 | Jackson |
| 2003/0236550 A1 | 12/2003 | Peterson |
| 2003/0236551 A1 | 12/2003 | Peterson |
| 2004/0010275 A1 | 1/2004 | Jacobs |
| 2004/0010276 A1 | 1/2004 | Jacobs |
| 2004/0015187 A1 | 1/2004 | Lendlein |
| 2004/0024420 A1 | 2/2004 | Lubbers |
| 2004/0028655 A1 | 2/2004 | Nelson |
| 2004/0030354 A1 | 2/2004 | Leung |
| 2004/0039415 A1 | 2/2004 | Zamierowski |
| 2004/0059377 A1 | 3/2004 | Peterson |
| 2004/0059378 A1 | 3/2004 | Peterson |
| 2004/0060409 A1 | 4/2004 | Leung |
| 2004/0060410 A1 | 4/2004 | Leung |
| 2004/0068293 A1 | 4/2004 | Scalzo |
| 2004/0068294 A1 | 4/2004 | Scalzo |
| 2004/0088003 A1 | 5/2004 | Leung |
| 2004/0093023 A1 | 5/2004 | Allen |
| 2004/0093028 A1 | 5/2004 | Ruff |
| 2004/0098051 A1 | 5/2004 | Fallin |
| 2004/0106949 A1 | 6/2004 | Cohn |
| 2004/0138683 A1 | 7/2004 | Shelton |
| 2004/0153153 A1 | 8/2004 | Elson |
| 2004/0167572 A1 | 8/2004 | Roth |
| 2004/0167575 A1 | 8/2004 | Roby |
| 2004/0193191 A1 | 9/2004 | Starksen |
| 2004/0193217 A1 | 9/2004 | Lubbers |
| 2004/0193257 A1 | 9/2004 | Wu |
| 2004/0226427 A1 | 11/2004 | Trull |
| 2004/0237736 A1 | 12/2004 | Genova |
| 2004/0254609 A1 | 12/2004 | Esplin |
| 2004/0260340 A1 | 12/2004 | Jacobs |
| 2004/0265282 A1 | 12/2004 | Wright |
| 2004/0267309 A1 | 12/2004 | Garvin |
| 2005/0004601 A1 | 1/2005 | Kong |
| 2005/0004602 A1 | 1/2005 | Hart |
| 2005/0033324 A1 | 2/2005 | Phan |
| 2005/0033367 A1 | 2/2005 | Leung |
| 2005/0034431 A1 | 2/2005 | Dey |
| 2005/0038472 A1 | 2/2005 | Furst |
| 2005/0059984 A1 | 3/2005 | Chanduszko |
| 2005/0065533 A1 | 3/2005 | Magen |
| 2005/0070959 A1 | 3/2005 | Cichocki, Jr. |
| 2005/0080455 A1 | 4/2005 | Schmieding |
| 2005/0085857 A1 | 4/2005 | Peterson |
| 2005/0096698 A1 | 5/2005 | Lederman |
| 2005/0106211 A1 | 5/2005 | Nelson |
| 2005/0113936 A1 | 5/2005 | Brustad |
| 2005/0119694 A1 | 6/2005 | Jacobs |
| 2005/0125020 A1 | 6/2005 | Meade |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson |
| 2005/0149118 A1 | 7/2005 | Koyfman |
| 2005/0154255 A1 | 7/2005 | Jacobs |
| 2005/0171561 A1 | 8/2005 | Songer |
| 2005/0177190 A1 | 8/2005 | Zamierowski |
| 2005/0182444 A1 | 8/2005 | Peterson |
| 2005/0182445 A1 | 8/2005 | Zamierowski |
| 2005/0197699 A1 | 9/2005 | Jacobs |
| 2005/0199249 A1 | 9/2005 | Karram |
| 2005/0203576 A1 | 9/2005 | Sulamanidze |
| 2005/0209542 A1 | 9/2005 | Jacobs |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff |
| 2005/0267532 A1 | 12/2005 | Wu |
| 2005/0277984 A1 | 12/2005 | Long |
| 2005/0283246 A1 | 12/2005 | Cauthen |
| 2006/0020272 A1 | 1/2006 | Gildenberg |
| 2006/0030884 A1 | 2/2006 | Yeung |
| 2006/0036266 A1 | 2/2006 | Sulamanidze |
| 2006/0058574 A1 | 3/2006 | Priewe |
| 2006/0058799 A1 | 3/2006 | Elson |
| 2006/0058844 A1 | 3/2006 | White |
| 2006/0064115 A1 | 3/2006 | Allen |
| 2006/0064116 A1 | 3/2006 | Allen |
| 2006/0064127 A1 | 3/2006 | Fallin |
| 2006/0079935 A1 | 4/2006 | Kolster |
| 2006/0085016 A1 | 4/2006 | Eremia |
| 2006/0089525 A1 | 4/2006 | Mamo |
| 2006/0089672 A1 | 4/2006 | Martinek |
| 2006/0111734 A1 | 5/2006 | Kaplan |
| 2006/0111742 A1 | 5/2006 | Kaplan |
| 2006/0122608 A1 | 6/2006 | Fallin |
| 2006/0135994 A1 | 6/2006 | Ruff |
| 2006/0135995 A1 | 6/2006 | Ruff |
| 2006/0142784 A1 | 6/2006 | Kontos |
| 2006/0193769 A1 | 8/2006 | Nelson |
| 2006/0194721 A1 | 8/2006 | Allen |
| 2006/0200062 A1 | 9/2006 | Saadat |
| 2006/0207612 A1 | 9/2006 | Jackson |
| 2006/0229671 A1 | 10/2006 | Steiner |
| 2006/0235445 A1 | 10/2006 | Birk |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin |
| 2006/0253126 A1 | 11/2006 | Bjerken |
| 2006/0257629 A1 | 11/2006 | Lendlein |
| 2006/0258938 A1 | 11/2006 | Hoffman |
| 2006/0272979 A1 | 12/2006 | Lubbers |
| 2006/0276808 A1 | 12/2006 | Arnal |
| 2006/0282099 A1 | 12/2006 | Stokes |
| 2006/0286289 A1 | 12/2006 | Prajapati |
| 2006/0287675 A1 | 12/2006 | Prajapati |
| 2006/0287676 A1 | 12/2006 | Prajapati |
| 2006/0293710 A1 | 12/2006 | Foerster |
| 2007/0005109 A1 | 1/2007 | Popadiuk |
| 2007/0005110 A1 | 1/2007 | Collier |
| 2007/0021779 A1 | 1/2007 | Garvin |
| 2007/0027475 A1 | 2/2007 | Pagedas |
| 2007/0038249 A1 | 2/2007 | Kolster |
| 2007/0065663 A1 | 3/2007 | Trull |
| 2007/0088391 A1 | 4/2007 | McAlexander |
| 2007/0135840 A1 | 6/2007 | Schmieding |
| 2007/0135843 A1 | 6/2007 | Burkhart |
| 2007/0151961 A1 | 7/2007 | Kleine |
| 2007/0156175 A1 | 7/2007 | Weadock |
| 2007/0167958 A1 | 7/2007 | Sulamanidze |
| 2007/0187861 A1 | 8/2007 | Genova |
| 2007/0208355 A1 | 9/2007 | Ruff |
| 2007/0208377 A1 | 9/2007 | Kaplan |
| 2007/0219587 A1 | 9/2007 | Accardo |
| 2007/0224237 A1 | 9/2007 | Hwang |
| 2007/0225642 A1 | 9/2007 | Houser |
| 2007/0225761 A1 | 9/2007 | Shetty |
| 2007/0227914 A1 | 10/2007 | Cerwin |
| 2007/0233188 A1 | 10/2007 | Hunt |
| 2007/0239206 A1 | 10/2007 | Shelton, IV |
| 2007/0257395 A1 | 11/2007 | Lindh |
| 2007/0282247 A1 | 12/2007 | Desai |
| 2008/0004603 A1 | 1/2008 | Larkin |
| 2008/0009838 A1 | 1/2008 | Schena |
| 2008/0009888 A1 | 1/2008 | Ewers |
| 2008/0009902 A1 | 1/2008 | Hunter |
| 2008/0027273 A1 | 1/2008 | Gutterman |
| 2008/0027486 A1 | 1/2008 | Jones |
| 2008/0046094 A1 | 2/2008 | Han |
| 2008/0058869 A1 | 3/2008 | Stopek |
| 2008/0066764 A1 | 3/2008 | Paraschac |
| 2008/0066765 A1 | 3/2008 | Paraschac |
| 2008/0066766 A1 | 3/2008 | Paraschac |
| 2008/0066767 A1 | 3/2008 | Paraschac |
| 2008/0077181 A1 | 3/2008 | Jones |
| 2008/0082113 A1 | 4/2008 | Bishop |
| 2008/0082129 A1 | 4/2008 | Jones |
| 2008/0086169 A1 | 4/2008 | Jones |
| 2008/0086170 A1 | 4/2008 | Jones |
| 2008/0109036 A1 | 5/2008 | Stopek |
| 2008/0132943 A1 | 6/2008 | Maiorino |
| 2008/0195147 A1 | 8/2008 | Stopek |
| 2008/0208358 A1 | 8/2008 | Bellamkonda |
| 2008/0215072 A1 | 9/2008 | Kelly |
| 2008/0221618 A1 | 9/2008 | Chen |

| | | | | | | |
|---|---|---|---|---|---|---|
| 2008/0234731 | A1 | 9/2008 | Leung | WO | WO9852473 | 11/1998 |
| 2008/0248216 | A1 | 10/2008 | Yeung | WO | WO9921488 | 5/1999 |
| 2008/0262542 | A1 | 10/2008 | Sulamanidze | WO | WO9905477 | 11/1999 |
| 2008/0281338 | A1 | 11/2008 | Wohlert | WO | WO0051658 | 9/2000 |
| 2008/0312688 | A1 | 12/2008 | Nawrocki | WO | WO03001979 | 1/2003 |
| 2009/0012560 | A1 | 1/2009 | Hunter | WO | WO03017850 | 3/2003 |
| 2009/0018577 | A1 | 1/2009 | Leung | WO | WO03045255 | 6/2003 |
| 2009/0043336 | A1 | 2/2009 | Yuan | WO | WO03103733 | 12/2003 |
| 2009/0076543 | A1 | 3/2009 | Maiorino | WO | WO03103972 | 12/2003 |
| 2009/0099597 | A1 | 4/2009 | Isse | WO | WO2004014236 | 2/2004 |
| 2009/0107965 | A1 | 4/2009 | D'Agostino | WO | WO2004030520 | 4/2004 |
| 2009/0112259 | A1 | 4/2009 | D'Agostino | WO | WO2004030704 | 4/2004 |
| 2009/0200487 | A1 | 8/2009 | Maiorino | WO | WO2004030705 | 4/2004 |
| 2009/0210006 | A1 | 8/2009 | Cohen | WO | WO2004112853 | 12/2004 |
| 2009/0226500 | A1 | 9/2009 | Avelar | WO | WO2006005144 | 1/2006 |
| 2009/0248066 | A1 | 10/2009 | Wilkie | WO | WO2006061868 | 6/2006 |
| 2009/0248067 | A1 | 10/2009 | Maiorino | WO | WO2006082060 | 8/2006 |
| 2009/0248070 | A1 | 10/2009 | Kosa | WO | WO2006099703 | 9/2006 |
| 2009/0250356 | A1 | 10/2009 | Kirsch | WO | WO2007053812 | 5/2007 |
| 2009/0259233 | A1 | 10/2009 | Bogart | WO | WO2007133103 | 11/2007 |
| 2009/0259251 | A1 | 10/2009 | Cohen | WO | WO2007145614 | 12/2007 |
| 2009/0287245 | A1 | 11/2009 | Ostrovsky | WO | WO2009068252 | 6/2009 |
| 2009/0299407 | A1 | 12/2009 | Yuan | WO | WO2009087105 | 7/2009 |
| 2009/0299408 | A1 | 12/2009 | Schuldt-Hempe | WO | WO2010052007 | 5/2010 |
| 2009/0306710 | A1 | 12/2009 | Lindh | | | |
| 2010/0023055 | A1 | 1/2010 | Rousseau | | | |
| 2010/0057123 | A1 | 3/2010 | D'Agostino | | | |
| 2010/0063540 | A1 | 3/2010 | Maiorino | | | |
| 2010/0071833 | A1 | 3/2010 | Maiorino | | | |
| 2010/0087855 | A1 | 4/2010 | Leung | | | |
| 2010/0101707 | A1 | 4/2010 | Maiorino | | | |
| 2010/0140115 | A1 | 6/2010 | Kirsch | | | |
| 2010/0294103 | A1 | 11/2010 | Genova | | | |
| 2010/0294104 | A1 | 11/2010 | Genova | | | |
| 2010/0294105 | A1 | 11/2010 | Genova | | | |
| 2010/0294106 | A1 | 11/2010 | Genova | | | |
| 2010/0294107 | A1 | 11/2010 | Genova | | | |
| 2010/0298637 | A1 | 11/2010 | Ruff | | | |
| 2010/0298867 | A1 | 11/2010 | Ruff | | | |
| 2010/0298868 | A1 | 11/2010 | Ruff | | | |
| 2010/0313723 | A1 | 12/2010 | Genova | | | |
| 2010/0313729 | A1 | 12/2010 | Genova | | | |
| 2010/0313730 | A1 | 12/2010 | Genova | | | |

FOREIGN PATENT DOCUMENTS

| | | |
|---|---|---|
| CN | 2640420 | 9/2004 |
| DE | 1810800 | 6/1970 |
| DE | 3227984 | 7/1982 |
| DE | 4302895 | 8/1994 |
| DE | 19618891 | 4/1997 |
| DE | 19833703 | 2/2000 |
| DE | 102005004317 | 6/2006 |
| EP | 0329787 | 8/1989 |
| EP | 0428253 | 5/1991 |
| EP | 0576337 | 12/1993 |
| EP | 0632999 | 1/1995 |
| EP | 0612504 | 11/1997 |
| EP | 0826337 | 3/1998 |
| EP | 0839499 | 5/1998 |
| EP | 0913123 | 5/1999 |
| EP | 0960600 | 12/1999 |
| EP | 1075843 | 2/2001 |
| FR | 2619129 | 2/1989 |
| FR | 2693108 | 1/1994 |
| GB | 267007 | 3/1927 |
| GB | 1091282 | 11/1967 |
| GB | 1428560 | 3/1976 |
| GB | 1506362 | 4/1978 |
| JP | 354116419 | 9/1979 |
| JP | 63288146 | 11/1988 |
| JP | 01113091 | 5/1989 |
| JP | 11332828 | 12/1999 |
| KR | 6013299 A | 2/2006 |
| NZ | 501224 | 3/2002 |
| NZ | 531262 | 6/2002 |
| RU | 2139690 | 10/1999 |
| SU | 1745214 | 7/1992 |
| SU | 1752358 | 8/1992 |
| WO | WO9606565 | 3/1996 |

OTHER PUBLICATIONS

International Search Report for PCT/US2008/060127 dated Sep. 23, 2008, 5 pages.

International Search Report for PCT/US2008/064921 dated Nov. 19, 2008, 3 pages.

International Search Report for PCT/US2008/075849 dated Mar. 18, 2009, 4 pages.

Singapore Search Report for Singapore Patent Application No. 200702625-5 dated Nov. 26, 2008, 7 pages.

Singapore Search Report for Singapore Patent Application No. 200702350-0 dated Nov. 26, 2008, 6 pages.

Singapore Search Report for Singapore Patent Application No. 200703688-2 dated Nov. 26, 2008, 7 pages.

European Search Report for EP07015905.8 dated Oct. 23, 2007, 2 pages.

European Search Report for EP10000629.5. dated Mar. 10, 2010, 4 pages.

European Search Report for EP10011871.0 dated Dec. 3, 2010, 2 pages.

European Search Report for EP10011868.6 dated Dec. 6, 2010, 2 pages.

European Search Report for EP10186592.1 dated Jan. 19, 2011, 2 pages.

Mason, M.L., "Primary and secondary tendon suture. A discussion of the significance of technique in tendon surgery", Surg Gynecol Obstet 70 (1940).

McKee, G.K., "Metal anastomosis tubes in tendon suture", The Lancet, May 26, 1945, 659-660.

Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.

Jennings et at, "A new technique in primary tendon repair", Surg Gynecol Obstet Nov. 1952;95(5):597-600.

Bunnell, S., "Gig pull-out suture for tendons", J Bone Joint Surg Am. Jul. 1954;36-A(4):850-1.

Verdan, Claude, "Primary Repair of Flexor Tendons", Journal of Bone and Joint Surgery Jun. 1960; 42(4):647-657.

Potenza, Austin, "Tendon Healing Within the Flexor Digital Sheath in the Dog: An Experimental Study", Journal of Bone & Joint Surgery Jan. 1962; 44A(1):49-64.

Pulvertaft, "Suture Materials and Tendon Junctures", American Journal of Surgery Mar. 1965; 109:346-352.

Buncke, Jr., H.J. et al., "The suture repair of one-millimeter vessels, micro-vascular surgery", Report of First Conference; Oct. 6-7, 1966; pp. 24-35 (esp. p. 34), USA.

McKenzie, A.R., "An Experimental Multiple Barbed Suture for the Long Flexor Tendons of the Palm and Fingers", Journal of Bone and Joint Surgery 1967; 49B(3): 440-447.

Zoltan, Janos, "Cicatrix Optimia: Techniques for Ideal Wound Healing", English language edition University Park Press, Baltimore, 1977:Chapter 3; pp. 54-55.

Han, Hongtao et al., "Mating and Piercing Micromechanical Structures for Surface Bonding Applications", Proceedings of the 1991 Micro Electro Mechanical Systems (MEMS >91), An Investigation of Micro Structures, Sensors, Actuators, Machines and Robots, Feb. 1991, pp. 253-258.

Malina, Martin et al., "Endovascular AAA Exclusion: Will Stents With Hooks and Barbs Prevent Stent-Graft Migration", Journal Endovascular Surgery 1998(5): 310-317.

Boenisch, U.W. et al., "Pull-our strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.

Sulamanidze, MD, M.A., et al., "Management of Facial Rhytids by Subcutaneous Soft Tissue Dissection", International Journal of Cosmetic Surgery and Aesthetic Dermatology, vol. 2(4), 2000, pp. 255-259.

Rofin-Baasel ,"Laser Marking on Plastic Materials", 2001.RB50.0, Rofin-Baasel Inc. 2001, 2 pages.

Semenov, G. M. et al., "Surgical Suture", 2001, pp. 12-13 and 92-98, Piter, Saint Petersburg.

Sulamanidze, M.A. et al., "Facial lifting with Aptos threads", International Journal of Cosmetic Surgery and Aesthetic Dermatology, 2001, pp. 1-8, No. 4.

Dattillo, Jr., Philip Paul, "Medical Textile: Application of an Absorbable Barbed Bi-Directional Surgical Suture", Journal of Textile and Apparel, Technology and Management, vol. 2(2), Spring 2002, pp. 1-5.

Lendlein, Andreas et al., "Biodegradable, Elastic Shape-Memory Polymers for Potential Biomedical Applications", Science vol. 296; May 31, 2002, pp. 1673-1676.

Leung, J. et al., "Barbed, Bi-directional Medical Sutures: Biomechanical Properties and Wound Closure Efficacy Study", 2002 Society for Biomaterials $28^{th}$ Annual Meeting Transactions, 1 page.

Sulamanidze, MD, M.A., et al., "Removal of Facial Soft Tissue Ptosis with Special Threads", Dermatol Surg 2002; 28; pp. 367-371.

Lendlein, Andreas et al., "Shape-Memory Polymers", Angew, Chem. Int. Ed. 2002, 41, 2034-2057.

Sulamanidze, MD, M.A., et al., "Clinical aspects of bloodless facelift using APTOS filaments", A.V. Vishnevsky Institute of Surgery, Bol=shaya Serpukhovskaya ul., 27, 113811 Moscow, Russia, (2002):24-34.

Sulamanidze, MD, M.A., et al., "Morphological foundations of facelift using APTOS filaments", Bolshaya Serpukhovskaya ul., 27, 113811 Moscow, Russia, (2002): 19-26.

Dattillo, Jr., Philip Paul, et al., "Tissue Holding Performance of Knotless Absorbable Sutures", 2003 Society for Biomaterials $29^{th}$ Annual Meeting Transactions, p. 101.

Ingle, Nilesh P et al., "Mechanical Performance and Finite Element Analysis of Bi-directional Barbed Sutures", Master of Science in Textile Technology & Management at North Carolina State University Aug. 2003, 126 pages.

Kuniholm, Jonathan Fairbank, et al., "Automated Knot Tying for Fixation in Minimally Invasive, Robot Assisted Cardiac Surgery", Master of Science in Mechanical & Aerospace Engineering at North Carolina State University May 2003, 71 pages.

Leung, J. et al., "Barbed Bi-directional Surgical Sutures: In Vivo Strength and Histopathology Evaluations", 2003 Society for Biomaterials $29^{th}$ Annual Meeting Transactions, p. 100.

Li, Yang Yang, et al., "Polymer Replicas of Photonic Porous Silicon for Sensing and Drug Delivery Applications", Science vol. 299; Mar. 28, 2003, pp. 2045-2047.

Leung, Jeffrey C. et al., "Barbed, Bi-Directional Surgical Sutures", International Conference & Exhibition on Healthcare & Medical Textiles, Jul. 8-9, 2003; 1-8.

Szarmach, Robin et al., "An Expanded Surgical Suture and Needle Evaulation and Selection Program by a Healthcare Resource Management Group Purchasing Organization", Journal of Long-Term Effects of Medical Implants 2003; 13(3); 155-170.

Ingle, Nilesh P et al., "Barbed Suture Anchoring Strength: Applicability to Dissimilar Polymeric Materials", College of Textiles, North Carolina State University, $7^{th}$ World Biomaterials Congress 2004, 1 page.

Leung, J. et al., "Performance Enhancement of a Knotless Suture via Barb Geometry Modifications", $7^{th}$ World Biomaterials Congress 2004, 1 page.

Wu, Woffles, "Barbed Sutures in Facial Rejuvenation", Aesthetic Surgery Journal 2004(24): 582-587.

Quill Medical, Inc., "Quill Medical's Novel-Self-Anchoring Surgical Suture Approved for Sale in Europe", Press Release; Research Triangle Park, N.C., May 10, 2004, 1 page.

Buckley, Patrick R., "Actuation of Shape Memory Polymer using Magnetic Fields for Applications in Medical Devices", Master of Science in Mechanical Engineering at the Massachusetts Institute of Technology Jun. 2003, 144 pgs.

Quill Medical, Inc., "Barbed sutures, wrinkle filters give patients more innovative, non-surgical options", Press Release of Program presented at American Society of Plastic Surgeons annual scientific meeting; Philadelphia, Oct. 9, 2004, 3 pages.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Surgical Specialties Corporation, "Wound Closure Catalog"; Summer 2005, 5 pages.

Rodeheaver, G.T. et al., "Barbed Sutures for Wound Closure: In Vivo Wound Security, Tissue Compatibility and Cosmesis Measurements", Society for Biomaterials $30^{th}$ Annual Meeting Transactions, 2005, 2 pages.

Belkas, J. S. et al., "Peripheral nerve regeneration through a synthetic hydrogel nerve tube", Restorative Neurology and Neuroscience 23 (2005) 19-29.

Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

De Persia, Raúl et al., "Mechanics of Biomaterials: Sutures After the Surgery", Applications of Engineering Mechanics in Medicine, GED-University of Puerto Rico, Mayaguez May 2005, p. F1-F27.

Scherman, Peter et al., "Sutures as longitudinal guides for the repair of nerve defects-Influence of suture numbers and reconstruction of nerve bifurcations", Restorative Neurology and Neuroscience 23 (2005) 79-85.

Sulamanidze, MD, M.A., et al., "Soft tissue lifting in the mid-face: old philosophy, new approach-internal stitching technique (APTOS NEEDLE)", Plastic and Aesthetic Surgery Clinic TOTAL SHARM, Moscow, Russia, (2005):15-29.

Bacci, Pier Antonio, "Chirurgia Estetica Mini Invasiva Con Fili Di Sostegno", Collana di Arti, Pensiero e Scienza; Minelli Editore—2006; 54 pgs.

Bellin, I. et al., "Polymeric triple-shape materials", Proceedings of the National Academy of Sciences of the United States of America Nov. 28, 2006; 2103(48):18043-18047.

Delorenzi, C.L., "Barbed Sutures: Rationale and Technique", Aesthetic Surg J. Mar. 2006 26(2): 223-229.

Gross, Alex, "Physician perspective on thread lifts", Dermatology Times Feb. 2006 27(2): 2 pages.

Khademhosseini, Ali et al., "Nanobiotechnology Drug Delivery and Tissue Engineering", Chemical Engineering Progress 102:38-42 (2006).

Murtha et al., "Evaluation of a Novel Technique for Wound Closure Using a Barbed Suture", Journal of the American Society of Plastic Surgeons 2006; 117(6); 1769-1780.

Ruff, Gregory, "Technique and Uses for Absorbable Barbed Sutures", Aesthetic Surgery Journal Sep./Oct. 2006; 26:620-628.

Behl, Marc et al., "Shape-Memory Polymers", Materials Today Apr. 2007; 10(4); 20-28.

Kaminer, M. et al., "ContourLift™: A New Method of Minimally Invasive Facial Rejuvenation", Cosmetic Dermatology Jan. 2007; 20(1): 29-35.

Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007;8(3):1018-1027.

Maitland et al., "Prototype laser-activated shape memory polymer foam device for embolic treatment of aneurysms", Journal of Biomedical Optics May/Jun. 2007 ;12(3): pp. 030504-1 to 030504-3.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Paul, Malcolm D. and Rui Avelar, "Quill™ SRS Techniques & Procedures A Novel Approach to Soft Tissue Approximation", Canada, Angiotech Pharmaceuticals, Inc., First Edition [8]2007: 20 pages.

Paul, Malcolm D. and Rui Avelar, "Quill™ SRS Techniques & Procedures A Novel Approach to Soft Tissue Approximation", Canada, Angiotech Pharmaceuticals, Inc., Second Edition [8]2008: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, [8] 2007-2009: 27 pages.

Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, [8] 2007-2010: 27 pages.

Dahlin, Lars, "Techniques of Peripheral Nerve Repair", Scandinavian Journal of Surgery 97: 310-316, 2008.

Madduri, Srinivas, et al., "Neurotrophic factors release from nerve conduits for peripheral axonal regeneration", European Cells and Materials vol. 16; Suppl. 1 (2008), p. 14.

Nie, Zhihong and Kumacheva, Eugenia, "Patterning surfaces with functional polymers", Nature Materials vol. 7(2008): 277-290.

Paul, Malcolm D., "Using Barbed Sutures in Open/Subperiosteal Midface Lifting", Aesthetic Surgery Journal 2006(26): 725-732.

Richert, Ludovic, et al., "Surface Nanopatterning to Control Cell Growth", Advanced Materials 2008(15): 1-5.

Tan Ee Lim et al., "A wireless, passive strain sensor based on the harmonic response of magnetically soft materials", Smart Materials and Structures 17 (2008): pp. 1-6.

Villa, Mark T. et al., "Barbed Sutures: A Review of Literature", Plastic and Reconstructive Surgery; Mar. 2008; vol. 121, No. 3; pp. 102e-108e.

Demyttenaere, Sebastian V. et al., "Barbed Suture for Gastrointestinal Closure: A Randomized Control Trial", Surgical Innovation; vol. 16, No. 3; Sep. 2009; pp. 237-242.

Einarsson, Jon I. et al., "Barbed Suture, now in the toolbox of minimally invasive gyn surgery", OBG Management; vol. 21, No. 9; Sep. 2009; pp. 39-41.

Paul, Malcolm D., "Bidirectional Barbed Sutures for Wound Closure: Evoluation and Applications", Journal of the American College of Certified Wound Specialists (2009) 1, 51-57.

Sulamanidze, Marlen et al., "APTOS Suture Lifting Methods: 10 Years of Experience", Clin Plastic Surg 36 (2009); pp. 281-306.

Ingle, N.P. et al., "Optimizing the tissue anchoring performance of barbed sutures in skin and tendon tissues", Journal of Biomechanics 43 (2010); pp. 302-309.

International Search Report for PCT/US2002/027525 dated Dec. 9, 2002, 3 pages.

European Search Report for EP107006258.3 dated May 4, 2007, 4 pages.

US 6,447,535, 09/2002, Jacobs (withdrawn)
US 6,503,260, 01/2003, Schaller (withdrawn)

* cited by examiner

SUTURE WITH A POINTED END AND AN ANCHOR END AND WITH EQUALLY SPACED YIELDABLE TISSUE GRASPING BARBS LOCATED AT SUCCESSIVE AXIAL LOCATIONS

CLAIM TO PRIORITY

This application is a continuation of U.S. application Ser. No. 11/968,494, filed Jan. 2, 2008, now U.S. Pat. No. 7,806,908, issued Oct. 5, 2010; which is a continuation of U.S. application Ser. No. 11/747,085, filed May 10, 2007, now abandoned; which is a continuation of U.S. application Ser. No. 10/420,119, filed Apr. 21, 2003, now U.S. Pat. No. 7,226,468, issued Jun. 5, 2007; which is a continuation of U.S. application Ser. No. 09/629,428, filed Jul. 31, 2000, now abandoned; which is a continuation of U.S. application Ser. No. 08/324,529, filed Oct. 18, 1994, now U.S. Pat. No. 6,241,747, issued Jun. 5, 2001; which is a continuation-in-part of U.S. application Ser. No. 08/055,989, filed May 3, 1993, now abandoned. All the above claimed priority applications are incorporated herein by reference in their entireties.

BACKGROUND OF THE INVENTION

1. Field of the Invention

This invention relates to a barbed tissue connector, and more particularly, to such a connector which can be used to quickly and effectively close a body wound.

2. Description of the Prior Art

Human wounds are typically repaired with a filament introduced into the tissue by a needle attached to one end. After piercing the opposing faces of the wound, the needle is removed, and the ends of the suture are tied together with at least three overhand knots. Such a technique requires considerable time and expertise on the part of the surgeon. There are also a number of other drawbacks to repairing a wound in this manner. For example, it is very difficult to use sutures to repair wounds where there is insufficient space to properly manipulate the suture, especially those wounds repaired using fiber optic visualization. The suture forms a loop as it is tied, and this loop constricts blood flow to the tissue in its confines, promoting necrosis of the wound margins. Further, if the needle's passage was noncircular, the tissue will be distorted as it is secured by the suture.

Alternatives to conventional sutures are known in the prior art. Staples, as shown, for example, in U.S. Pat. No. 4,994,073, to Green, are often used for approximating the superficial layer of the wound. Staples, however, are generally unsuitable for deeper layers of tissue.

The patent to Alcamo, U.S. Pat. No. 3,123,077, discloses a roughened suture which can be passed through tissue in one direction, but resists movement in the opposite direction. The Alcamo suture, however, still must be sewn, as by a conventional technique, and the trailing end must be secured with knots. Thus, although there is less slippage of the suture in the wound, most of the disadvantages of sutures noted above are also found in the Alcamo suture.

The patent to Tanner, U.S. Pat. No. 3,716,058, discloses a relatively rigid suture with one or more barbs on opposite ends of an arcuate body. One disadvantage of the Tanner suture is that the rigid barbs, which protrude from the suture as it is inserted, will lacerate tissue and prevent retrograde repositioning. Further, since the barbs are only placed at the ends of the suture, the forces applied to the tissue by the barbs will be limited to a relatively small area; this substantially increases the pressure on the blood vessels ensnared by a barb and severely restricts blood flow to the area.

It will be seen from the foregoing that there is a need for a tissue connector which can be placed more expeditiously than sutures, is self-retaining, obviates distortion of the tissue, can close tissue inaccessible to conventional procedures, and which preserves blood flow by broadly distributing the retention force.

SUMMARY OF THE INVENTION

It is an object of the present invention to overcome the aforementioned problems in the prior art and to provide an improved tissue connector.

In accordance with the present invention there is provided a barbed tissue connector comprising: an elongated body having a point formed on one end, the body being formed of a material sufficiently hard for the point to pierce tissue and enable the connector to be inserted in tissue when a substantially axial force is applied to the body; and a plurality of barbs projecting from the body, the barbs being disposed around the periphery of the body along a length of the body which extends from adjacent the one end to a predetermined location on the body, the barbs being configured such that they are yieldable in a direction toward the body and are generally rigid in an opposite direction, and the barbs being sufficiently resilient to return to a predetermined position after deflection therefrom.

In one embodiment of the present invention, the barbed tissue connector includes an elongated body and a plurality of barbs which are disposed in a helical pattern on the body and extend from a pointed end of the connector to a predetermined location on the body. Each barb includes a first side, which forms an obtuse angle with the body, and a second side which forms an acute angle with the body. The body is substantially rigid and sufficiently resilient to return to a predetermined position after deflection therefrom. When the connector is inserted in tissue to repair a wound, the pointed end pierces tissue and the barbs yield toward the body to facilitate entry of the connector.

When the connector has been placed in a desired position in tissue, the barbs strongly resist movement away from this position. The connector can be inserted by gripping the connector in the hand and pushing the connector into the tissue, or the connector can be inserted by means of an inserting device which is withdrawn when the connector is in place.

A principal advantage of the barbed tissue connector of the present invention is that it permits a surgeon to rapidly and securely attach the edges of a wound in human tissue without the necessity for threading and tying numerous individual stitches or for the use of a complicated or elaborate tool to insert the connector. The connector is configured to minimize damage to tissue when inserted and to minimize scarring or tissue necrosis across the wound. The connector is capable of insertion into the faces of a wound, can connect tissue at the bottom of a deep wound, and can connect tissue which is inaccessible to a staple. Finally, the connector of the present invention can be inserted quickly and accurately by a surgeon who only has access to tissue from a small opening or from only one direction, as, for example, during an endoscopic procedure.

Other features and advantages will become apparent upon reference to the following description of the preferred embodiment when read in light of the attached drawings.

DESCRIPTION OF THE PREFERRED EMBODIMENTS

The present invention allows a surgeon to rapidly and securely attach the edges of a wound in human tissue without the necessity for threading and tying numerous individual stitches or for using a complicated or elaborate tool. As used herein, the term "wound" means an incision, laceration, cut, or other condition where suturing, stapling, or the use of another tissue connecting device might be required.

Figure 1:
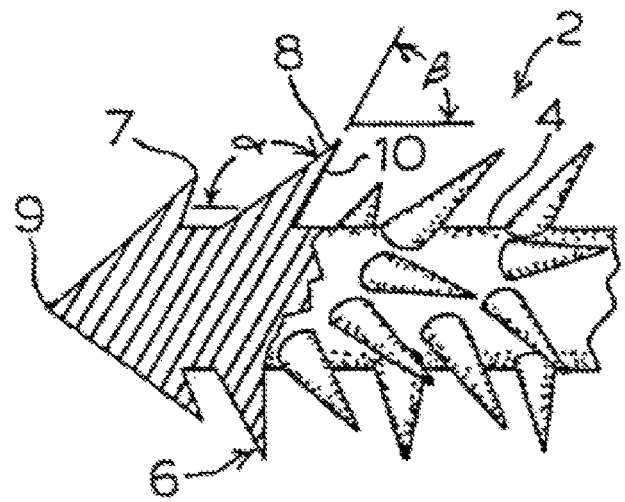
FIG. 1 is a side view of the connector of the present invention, with a section broken away to more clearly show the arrangement of the barbs.
Figure 2:
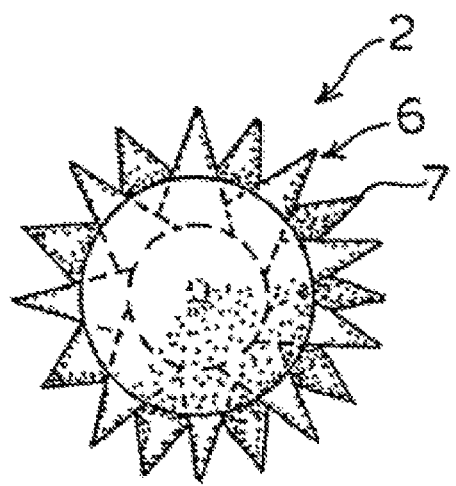
FIG. 2 is an end view of the connector shown in FIG. 1.

With reference to FIGS. 1 and 2, there is shown a barbed tissue connector 2 constructed in accordance with the present invention. Connector 2 includes a body 4 which is generally circular in cross section and a plurality of closely-spaced barbs 6 which extend around the periphery of the body 4. A pointed end 9 is formed on the body 4 to facilitate penetration of the connector 2 into tissue. The body 4 preferably has sufficient dimensional stability to assume a substantially rigid configuration during use and is sufficiently resilient to return to a predetermined shape after deflection therefrom. In some applications, it may be desirable for the body 4 to be flexible and substantially nonresilient so that the shape of an inserted connector will be determined by surrounding tissue.

Barbs 6 serve to hold the connector in tissue and resist retraction of the connector from the tissue. The barbs 6 can be arranged in any suitable pattern, for example, in a helical pattern as shown in FIG. 1. In a helical pattern of barbs 6, it is preferable that the number of barbs occupying one revolution not be an integer, thereby avoiding parallel axial rows of barbs; such an arrangement provides a more uniform distribution of forces on the tissue and lessens the tendency of an inserted connector 2 to cut through tissue. If the number of barbs in one revolution is not an integer, the barbs in successive revolutions will be offset, as shown in FIG. 2, and the amount of offset will determine which barbs are in axial alignment. For example, if the barbs in successive revolutions are offset by ½ barb, the barbs in every second revolution will be in axial alignment, and by extension, if the barbs in each successive revolution are offset by 1/x barb, the barbs in every x revolution will be in axial alignment.

As shown in FIG. 1, each barb 6 includes a first side 8 which forms an obtuse angle alpha with the body 4 and a second side 10 which forms an acute angle beta with the body 4. Each barb 6 tapers to a point 7, and the amount of difference between the angle alpha of side 8 and angle beta of side 10 will control the amount of taper in the barb 6. A barb 6 which tapers from a broad base to a narrow tip can be effective in resisting retraction, yet will yield toward the body 4 during insertion to reduce the effort and tissue damage associated with insertion of the connector 2. The barbs 6 can be generally conical, as shown in FIG. 1, or they can be any other shape which will function in substantially the same manner as the conical barbs.

The configuration of barbs 6 and the surface area of the barbs can vary depending upon the tissue in which the connector 2 is used. The proportions of the barbs 6 can remain relatively constant while the overall length of the barbs and the spacing of the barbs are determined by the tissue being connected. For example, if the connector 2 is intended to be used to connect the edges of a wound in skin or tendon, each barb 6 can be made relatively short to facilitate entry into this rather firm tissue. If the connector 2 is intended for use in fatty tissue, which is relatively soft, the barbs can be made longer and spaced farther apart to increase the holding ability in the soft tissue. As shown in FIG. 1, the barbs 6 on connector 2 have a uniform unidirectional configuration, that is, the barbs 6 are uniformly spaced on body 4 and all the sides 8 are oriented in the same direction, facing pointed end 9. Connector 2 can be inserted into tissue with the sides 8 of each barb 6 facing in the direction of motion. Connector 2 will prevent movement of tissue in the direction in which it was inserted. A pair of connectors 2 inserted adjacent to each other and in opposite directions will prevent movement of tissue in either direction across a wound.

Connector 2 can be formed of a material sufficiently hard for point 9 to pierce tissue and enable the connector to be inserted in tissue when a substantially axial force is applied to body 4. Connector 2 is preferably composed of a bioabsorbable compound, such as a polyglycolic acid or polylactic acid polymer or copolymer. The use of a bioabsorbable material eliminates the necessity of removing the connector from the patient, which can be a painful and possibly dangerous process. Connector 2 can be formed, for example, by injection molding.

In one representative example of connector 2 for use in muscular tissue, the body 4 is formed from polyglycolic acid, has a length of 1 to 5 cm, and a diameter of about 1 mm. The diameter of a circle extending around points 7 of barbs 6 will be about 3 mm, and the barbs are spaced apart from each other on body 4 by a distance of 1 mm. Side 8 forms an angle of 135 degrees with the body 4 and side 10 forms an angle of 75 degrees with the body 4.

Figure 3:
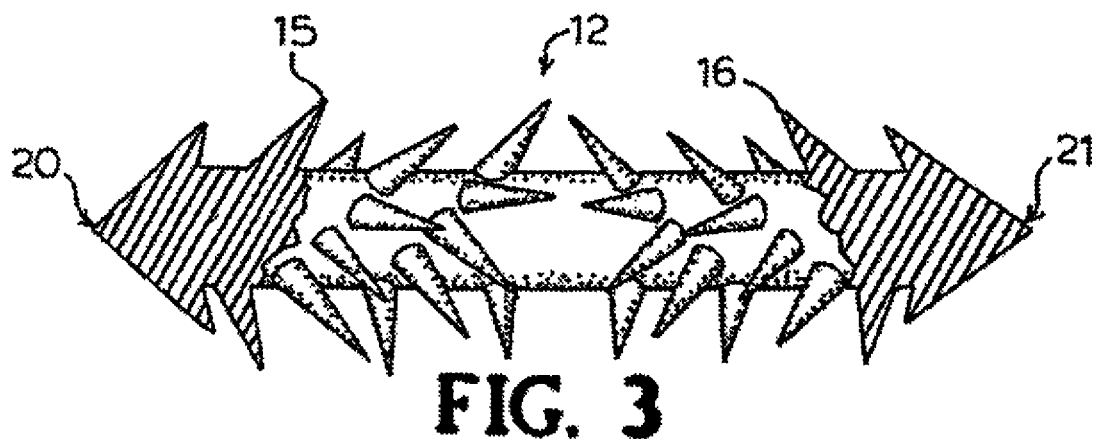
FIG. 3 is a side view of another embodiment of the present invention, with a section of a connector broken away.

In FIG. 3, there is shown a second embodiment of the present invention in which barbs 16 are arranged in a uniform bidirectional configuration on a barbed tissue connector 12. Barbs 16 are constructed in the same manner as barbs 6 on connector 2. A first set of barbs 15 on connector 12 are arranged in a helical pattern and face a pointed end 20, and a second set of barbs 16 on connector 12 are arranged in a helical pattern and face a pointed end 21. Each of the pointed ends 20, 21 should be sufficiently hard and sharp to easily penetrate tissue in which the connector is to be used. Connector 12 is particularly suitable for applications where the edges of a wound are prone to separate. Connector 12 can be used by inserting one of the ends, for example end 20, into a first side of a wound (not shown), spreading the wound slightly to expose the second side of the wound, inserting the end 21 of the connector 12 into the second side of the wound, and then pressing the edges of the wound together. The barbs 15 and 16 on the ends of the connector 12 will grasp the tissue on each side of the wound and prevent the edges of the wound from spreading.

Figure 4:
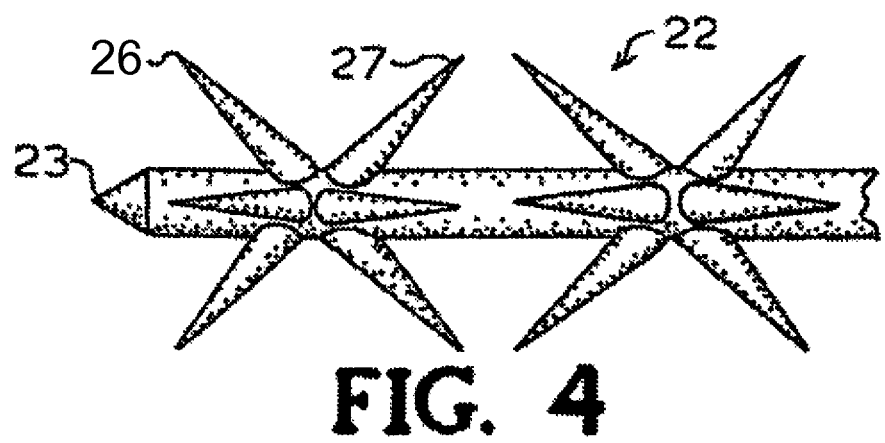
FIG. 4 is a side view of another embodiment of the present invention.

With reference to FIG. 4, there is shown another embodiment of the present invention in which a barbed tissue connector 22 has a nonuniform bidirectional configuration. Connector 22 comprises a pointed end 23 and one or more barbs 26 facing a first direction which alternate with one or more barbs 27 facing a second direction. At each axial location, there can be a number, e.g. 4-9, of circumferentially-spaced barbs 26 or 27. To insert connector 22 into tissue, the surgeon would use an inserting device 80 as described below. The arrangement of barbs 26, 27 on connector 22 would prevent any localized movement of tissue relative to the connector in an axial direction.

Figure 5:
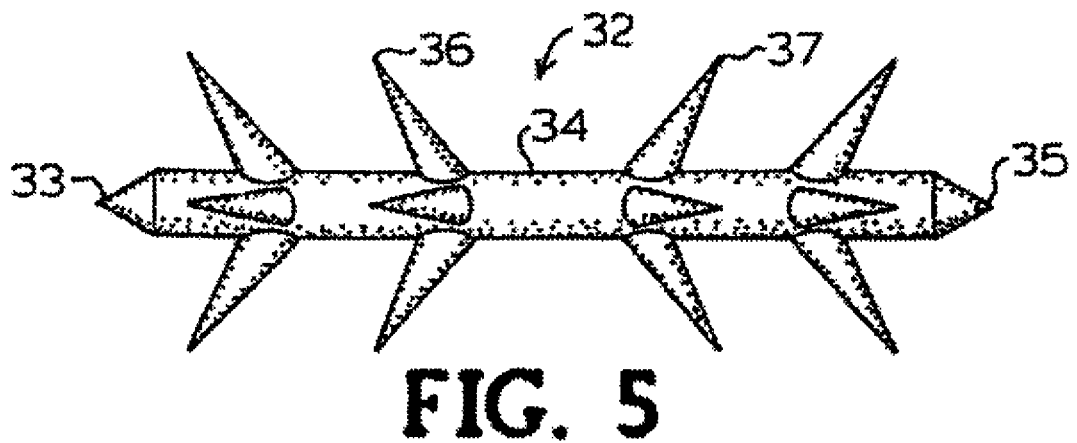
FIG. 5 is a side view of another embodiment of the present invention.

With reference to FIG. 5, there is shown another embodiment of the present invention in which a barbed tissue connector 32 has a uniform bidirectional configuration. Connector 32 comprises a body 34 having pointed ends 33 and 35. A plurality of axially-spaced barbs 36 adjacent pointed end 33 face toward end 35, and a plurality of axially-spaced barbs 37 adjacent pointed end 35 face toward end 33. Barbs 36 and 37 can be circumferentially-spaced around body 34 at each axial location, or the barbs 36 and 37 can be of the same construction and arranged in the same pattern as barbs 6 on connector 2. To insert a connector 32, the surgeon would use an inserting device 80 as described below. If the body 34 of the connector 32 is sufficiently rigid, the connector 32 would prevent tissue retained by the barbs 36 from moving toward end 35 and tissue retained by barbs 37 from moving toward end 33. It will be apparent that only one end of connector 32 needs to be pointed; two pointed ends are preferable, however, so that the surgeon does not have to take the time to insure that connector 32 is oriented in the inserting device 80 with a pointed end protruding from the inserting device.

Figure 6:
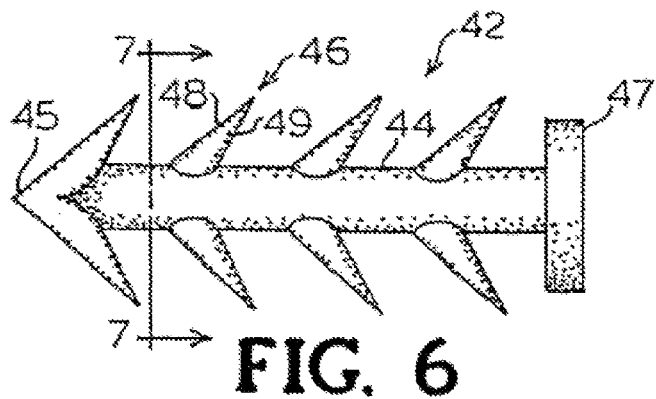
FIG. 6 is a side view of another embodiment of the present invention.
Figure 7:
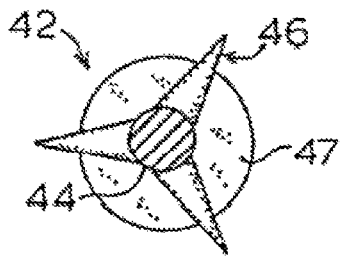
FIG. 7 is a sectional view taken along the line 7-7 in FIG. 6.

With reference to FIGS. 6 and 7, there is shown another embodiment of the present invention in which a barbed tissue connector 42 comprises a body 44 having a pointed end 45 for penetration into tissue. A head 47 is formed on an opposite end of body 44. A plurality of circumferentially-spaced barbs 46 are formed on body 44 at each of a number of axial locations. As shown in FIG. 7, three barbs 46 are formed at each axial location; however, more or less than three barbs 46 could be used for certain applications. Barbs 46 include a first side 48 formed at an obtuse angle to the body 44 and a second side 49 which projects from body 44 at an acute angle. The connector 42 can be forced into tissue by applying a force to the head 47. The connector 42 can be applied by hand, or it can be inserted using an inserting device 80 as described below.

The connector 42 can be formed entirely of a bioabsorbable material, or the head 47 and the body 44 can be composed of different materials. For example, the body 44 can be composed of a bioabsorbable material, and the head 47 can be composed of metal for superior strength and to facilitate insertion of the connector 42. Head 47 can be made flat, as shown in FIG. 6, or the head can be formed by a single ring of barbs (not shown) facing in a direction opposite to that of the barbs 46.

In use, a series of connectors 42 can be inserted into tissue, such as along the edges and in the field of a skin graft. After an adequate amount of time has passed for the wound to heal, the tissue beneath each head 47 could be depressed slightly to permit the head 47 to be cut from the body 44. The tissue would then rise up over the cut end of the body. Such a process would reduce scarring which could result from a long-term projection of the body 44 through tissue and would eliminate the necessity to remove connectors 42 from the patient.

Figure 8:
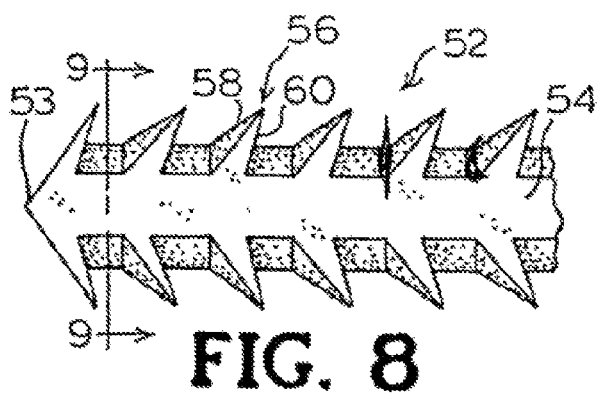
FIG. 8 is a side view of another embodiment of the present invention.
Figure 9:
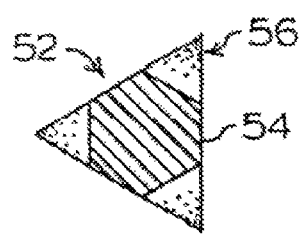
FIG. 9 is a sectional view taken along the line 9-9 in FIG. 8.

With reference to FIGS. 8 and 9, there is shown another embodiment of the present invention in which a barbed tissue connector 52 has a uniform unidirectional configuration. Connector 52 comprises a body 54 having a non-circular cross-sectional shape. Body 54 includes a plurality of barbs 56 which are generally triangular in cross section and are equally spaced around the periphery of the body at a series of axial locations. Each of the barbs 56 includes a first side 58 disposed at an obtuse angle to body 54 and a second side 60 disposed at an acute angle to the body. Body 54 includes a pointed end 53 to facilitate entry in tissue. Use of a non-circular cross-sectional shape increases the surface area of the connector 52 and facilitates the formation of the multiple barbs on the connector. For example, barbs 56 can be formed on a piece of stock having a triangular cross section by removing material at successive axial locations from the three edges of the stock. It will be apparent that a similar process could be used to form barbs on stock of a different cross section (not shown), for example, a rectangular or hexagonal cross section.

Figure 10:
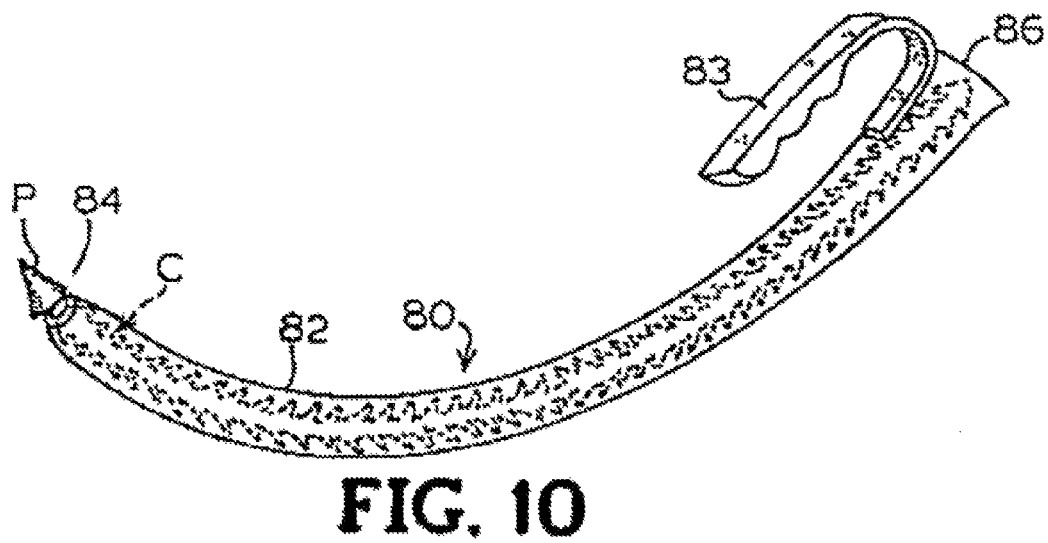
FIG. 10 is a perspective view of an inserting device for use with a barbed tissue connector of the present invention.
Figure 11:
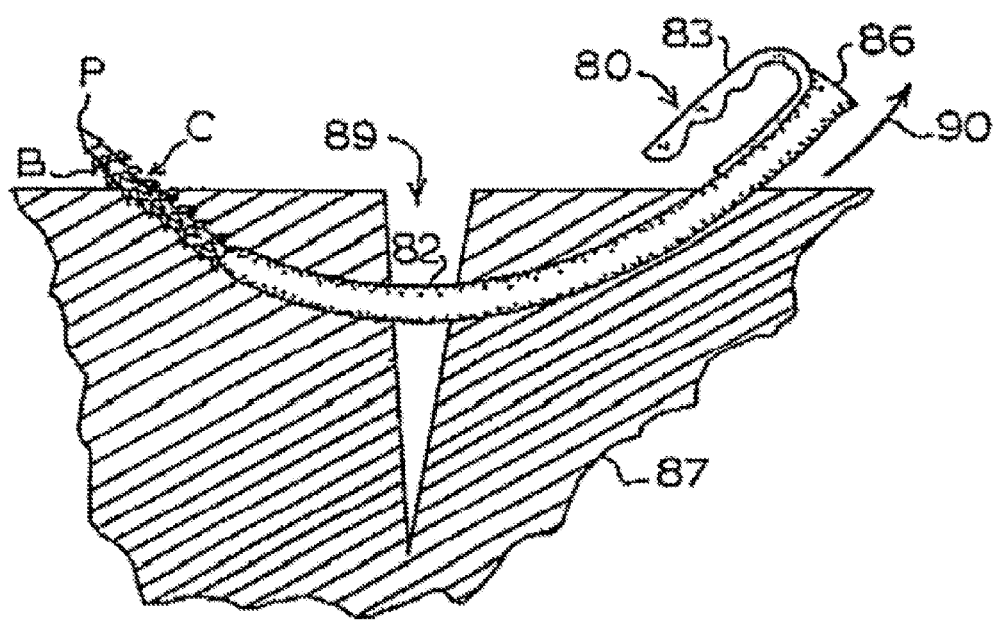
FIG. 11 is a view showing the inserting device and connector in a wound.

In the use of the disclosed connectors, such as connectors 2 and 42, the surgeon can grip the connector in one hand and push the connector into the tissue. As an alternative to directly inserting the connectors into the tissue, the surgeon can use an inserting device 80 as shown in FIGS. 10 and 11. The inserting device 80 comprises a circular tubular body 82. The tubular body 82 can be generally arcuate in an axial direction, and the body 82 is sufficiently long to contain at least a portion of a barbed tissue connector C. Device 80 has an inwardly tapered leading end 84 and an outwardly tapered, or flared, trailing end 86. A handle 83 is provided on body 82 adjacent trailing end 86 to enable the surgeon to manipulate the inserting device 80.

In order to facilitate entry of the connector C and the device 80 into tissue, a connector C is positioned in tubular body 82 with a pointed end P of the connector C extending from leading end 84. In a preferred embodiment, the interior diameter of the body 82 is made slightly smaller than the outside diameter of the connector C so that the barbs B of a connector C in the body 82 will press against the body 82; as a result, the connector C will be retained in the body 82 during insertion in tissue with the point P properly positioned outside of the body 82. The connector can also be positioned in body 82 with a barb B outside of body 82 to insure that the connector C will not be pushed back in the body 82 during insertion. In one application of device 80, the surgeon inserts the body 82 having connector C therein into the patient's tissue 87 until the connector C reaches a desired position, for example, the position shown in FIG. 11. Device 80 is then withdrawn in the direction of arrow 90, and a barb, or barbs, B on the connector C penetrates and catches the tissue 87 to hold the connector C in the inserted position.

Use of the inserting device 80 is particularly recommended when the connector C includes multiple barbs facing more than one direction, such as connectors 22 and 32, or when the connector is too flexible for insertion without additional support.

While the present invention has been described with respect to certain preferred embodiments thereof, it is to be understood that numerous variations in the details of construction, the arrangement and combination of parts, and the type of materials used may be made without departing from the spirit and scope of the invention.

What is claimed is:
1. A tissue connector comprising:
an elongated body with a generally circular cross-section and being flexible and substantially nonresilient, the elongated body having a first end, a second end, a periphery, and a plurality of barbs extending from said periphery of the elongated body, wherein said barbs comprise a first side forming an obtuse angle with the elongated body and a second side forming an acute angle with the elongated body, said barbs having a constant proportion as they extend along a portion of said body, where the first side of said barbs face the first end of the elongated body, the barbs being configured such that the barbs are yieldable in a direction toward the elongated body when the tissue connector is moved through tissue in a direction of the first end, and are generally rigid when the tissue connector is moved in an opposite direction toward the second end; and wherein a barb is located at each of a plurality of axial locations of said body, a first side of each barb facing said first end, and barbs are about equally and uniformly circumferentially spaced about the periphery of the body in a helical pattern and are oriented in the same direction, and said first end including a pointed end and being sufficiently hard to pierce tissue, and said second end including a head.

2. The tissue connector of claim 1 wherein:
said head includes an anchor which is adapted to prevent tissue from going past said head.

3. The tissue connector of claim 1 wherein:
said head includes an anchor.

4. The tissue connector of claim 1 wherein:
said head is larger than a diameter of said elongated body and said head is adapted to prevent tissue from going past said head.

5. The tissue connector of claim 1 wherein:
said head is adapted to have tissue located below said head.

6. The tissue connector of claim 1 wherein:
said head is adapted to be located above tissue.

7. The tissue connector of claim 1 and including:
a cannula through which said tissue connector is adapted to be deployed into tissue.

8. The tissue connector of claim 1 and including:
a cannula through which said tissue connector is adapted to be deployed into tissue during an endoscopic procedure.

9. The tissue connector of claim 1 wherein:
said barbs are arranged on said periphery and adapted to lessen a tendency of said connector to damage tissue.

10. The tissue connector of claim 1 wherein:
said barbs are conical.

11. The tissue connector of claim 1 wherein:
said connector is made of a bioabsorbable material.

12. The tissue connector of claim 1 wherein:
said connector is formed of a first material and a second material with superior strength to said first material.

13. The tissue connector of claim 1 wherein:
said barbs are located in staggered positions about said periphery of said connector.

14. The tissue connector of claim 1 wherein:
said pointed end is free of barbs.

15. A tissue connector comprising:
a flexible and substantially nonresilient elongated body with a generally circular cross-section having a first end, a second end, a periphery, and a plurality of barbs extending from said periphery of the elongated body, wherein said barbs comprise a first side forming an obtuse angle with the elongated body and a second side forming an acute angle with the elongated body, said barbs having a constant proportion as they extend along a portion of said body, and wherein the first side of the barbs face said first end of the elongated body, the barbs being configured such that the barbs are yieldable in a direction toward the elongated body when the tissue connector is moved through tissue in a direction of the first end, and are generally rigid when the tissue connector is moved through tissue in an opposite direction toward the second end; and wherein a barb is located at each of a plurality of axial locations of said body, a first side of each barb facing said first end, and barbs are about equally and uniformly circumferentially spaced in a helical pattern and are oriented in a same direction about the periphery of the body, and said first end including a pointed end and being sufficiently hard to pierce tissue, and said second end including a head; and said head is larger than a diameter of said elongated body and said head is adapted to prevent tissue from going past said head such that said head is adapted to be located adjacent to tissue.

16. The tissue connector of claim 15 wherein:
said connector is made of a bioabsorbable material.

* * * * *